US007012149B2

(12) United States Patent
Burdick et al.

(10) Patent No.: US 7,012,149 B2
(45) Date of Patent: Mar. 14, 2006

(54) PROCESS FOR THE PRODUCTION OF (−)-EPIGALLOCATECHIN GALLATE

(75) Inventors: David Carl Burdick, Binningen (CH); Heinz Egger, Zürich (CH); Andrew George Gum, Basel (CH); Ingo Koschinski, Waldshut-Tiengen (DE); Elena Muelchi, Münchenstein (CH); Isabelle Prevot-Halter, St. Louis (FR)

(73) Assignee: DSM IP Assets B.V., Heerlen (NL)

( * ) Notice: Subject to any disclaimer, the term of this patent is extended or adjusted under 35 U.S.C. 154(b) by 267 days.

(21) Appl. No.: 10/246,112

(22) Filed: Sep. 18, 2002

(65) Prior Publication Data

US 2003/0083270 A1 May 1, 2003

Related U.S. Application Data

(63) Continuation of application No. 09/638,926, filed on Aug. 15, 2000, now abandoned.

(30) Foreign Application Priority Data

Aug. 16, 1999 (EP) ............................................ 99116032

(51) Int. Cl.
C07D 311/04 (2006.01)
C07D 311/26 (2006.01)
C07D 311/62 (2006.01)

(52) U.S. Cl. ....................... 549/399; 424/725; 424/729; 424/732; 424/738; 514/23; 514/27; 514/54; 514/456; 549/400; 549/401; 549/403

(58) Field of Classification Search ................. 424/725, 424/729, 732, 738; 549/399, 400, 401, 403; 514/27, 54, 23, 456
See application file for complete search history.

(56) References Cited

U.S. PATENT DOCUMENTS

| | | | |
|---|---|---|---|
| 4,613,672 A | 9/1986 | Hara | |
| 4,806,379 A | 2/1989 | Goers et al. | 426/650 |
| 5,021,253 A | 6/1991 | Dawson-Ekeland et al. | 426/422 |
| 5,043,100 A | 8/1991 | Chang et al. | 252/398 |
| 5,391,568 A | 2/1995 | Chung | 514/456 |
| 5,804,567 A | 9/1998 | Cheng et al. | 514/49 |
| 5,879,733 A | 3/1999 | Ekanayake et al. | |
| 6,210,679 B1 | 4/2001 | Bailey et al. | 424/195.1 |
| 6,214,868 B1 | 4/2001 | Ahn et al. | |
| 6,254,898 B1 | 7/2001 | Bragaglia | |

FOREIGN PATENT DOCUMENTS

| | | |
|---|---|---|
| CN | 1067359 | 12/1992 |
| EP | 0 167 399 | 1/1986 |
| EP | 0 547 370 A2 | 6/1993 |
| JP | 51-104096 | 9/1976 |
| JP | 62-61569 | 3/1987 |
| JP | 02-311474 A2 | 12/1990 |
| JP | 4-77424 | 3/1992 |
| JP | 06-009607 A2 | 1/1994 |
| JP | 07-070105 A2 | 3/1995 |
| JP | 10-67771 | 3/1998 |
| WO | WO 96/28178 | 9/1996 |

OTHER PUBLICATIONS

Yang, et al., "Tea and Cancer," *Journal of the National Cancer Institute*, vol. 85, No. 13 (1993).
Amarowicz, et al., "Antioxidant Activity of Green Tea Catechins in a β–Carotene–Linoleate Model System," *Journal of Food Lipids*, vol. 2, pp. 47–56 (1995).
Tamagawa, et al., "Antioxidative Activity of Polyphenol Extracts from Barley Bran," *J. Jap. Soc. Food. Sci. Tech.*, vol. 44, No. 7, pp. 512–515 (1997).
Derwent English language abstract of JP 62–61569 (Document B4 above).
Derwent English language abstract of JP 10–67771 (Document B5 above).
Derwent English language abstract of JP 4–77424 (Document B6 above).
Derwent English language abstract of JP 51–104096 (Document B7 above).
Derwent English language abstract of CN 1067359 (Document B8 above).
Chemical Abstracts, vol. 111, No. 17, abstract No. 6208f (1989).
Amarowicz, et al., "A Rapid Chromatographic Method for Separation of Individual Catechins From Green Tea," *Food Research International*, vol. 29, No. 1, pp. 71–76 (1996).
Ozawa, "Separation of the Components in Black Tea Infusion by Chromatography on Toyopearl," *Agric. Biol. Chem.*, vol. 46(4), pp. 1079–1081 (1982).
Yang, et al., "Tea and Cancer," *Journal of the National Cancer Institute*, vol. 85, No. 13 (1993).
Amarowicz, et al., "Antioxidant Activity of Green Tea Catechins in a β–Carotene–Linoleate Model System," *Journal of Food Lipids*, vol. 2, pp. 47–56 (1995).
Tamagawa, et al., "Antioxidative Activity of Polyphenol Extracts from Barley Bran," *J. Jap. Soc. Food. Sci. Tech.*, vol. 44, No. 7, pp. 512–515 (1997).
"Diaion, Ion–Exchange Resin Synthetic Adsorbent, Manual I, Basics," Mitsubishi Chemical Corp., cover and copyright pages and pp. 30–33 (May 1, 1994) and rough, partial translation.
"Ion–Exchange Resin (Amberlite) Technology and Application (Basics)," Revised Ed. vol. 2, Organo Corp, cover and copyright pages and pp. 3–6 and 79–85 (Mar. 31, 1997) and rough partial translation.
Delphion Publication– English language Abstract of JP 07–070105 A2 (document B9 above).
Delphion Publication– English language Abstract of JP 02–311474 A2 (document B10 above).
Delphion Publication– English language Abstract of JP 06–009607 A2 (document B11 above).

Primary Examiner—Herbert J. Lilling
(74) Attorney, Agent, or Firm—Bryan Cave LLP

(57) ABSTRACT

A process is provided for making (−)-epigallocatechin gallate (EGCG) by subjecting a green tea extract to chromatography on a macroporous polar resin, eluting EGCG from the resin with a polar elution solvent, optionally concentrating the eluate, optionally regenerating the resin by desorbing the remaining catechins, and optionally concentrating the desorbed catechins.

23 Claims, No Drawings

PROCESS FOR THE PRODUCTION OF (−)-EPIGALLOCATECHIN GALLATE

This is a Continuation of U.S. application Ser. No. 09/638,926, filed Aug. 16, 2000 abandoned.

FIELD OF THE INVENTION

The present invention relates to a process for the production of (−)-epigallocatechin gallate (EGCG). The invention particularly relates to a process for the production of EGCG by separation from tea catechins by treatment with a macroporous polar resin.

BACKGROUND OF THE INVENTION

Leaves of the green tea plant camellia sinensis contain up to 36% polyphenols on a dry weight basis, however, their composition varies with climate, season, variety and state of maturity. Green tea catechins are the predominant group of green tea polyphenols. Examples of catechins are (−)-epicatechin (EC), (−)-epigallocatechin gallate (EGCG), epigallocatechin (EGC) and epicatechin gallate (ECG).

EGCG is the most interesting compound among the above mentioned catechins because it exhibits a strong antioxidant effect. Furthermore, it has been demonstrated that EGCG has an antimutagenic effect, an antibacterial effect, and a beneficial effect on cholesterol level in blood. The other catechins present in green tea are much less effective compared to EGCG. Green tea also contains other components such as caffeine, proteins, pectins, and/or metal ions which might not be desirable.

There is, therefore, a need to isolate EGCG in a pure form in high yield by a simple and economical process. However, the structural similarities of the various green tea catechins make the separation of the individual catechins difficult. Furthermore, the catechins in green tea are normally accompanied by caffeine, which is present in an amount up to 4% of the dry mass of the green tea leaves. Caffeine is known to associate with the catechins and is not trivial to remove.

The production of green tea extracts is well known in the art. Ekanayake, et al., U.S. Pat. No. 5,879,733 ("Ekanayake '733") describes the preparation of a green tea extract having improved clarity and color. The green tea extract is obtained by treating the extract at a temperature in the range of 25° C. to 60° C. with an amount of a food grade cation exchange resin effective to remove metal cations present in the extract. The treated extract is then contacted with a nanofiltration membrane. However, the process described in Ekanayake '733 is not suitable to separate EGCG from a mixture of tea catechins.

Hara, U.S. Pat. No. 4,613,672 ("Hara '672") describes a process for the preparation of pure EGCG which process includes the following steps: Tea leaves are extracted with hot water or with aqueous solutions of 40–75% methanol, 40–75% ethanol or 30–80% acetone. The obtained extract is washed with chloroform, and the washed extract is dissolved in an organic solvent. The organic solvent is distilled off, and the concentrated extract component is subjected to high speed liquid chromatography using a reverse-phase partition column with a developer of acetone/tetrahydrofuran/water (0–25:0–35:65–85, vol %), whereby each of (−) epicatechin, (−) epigallocatechin, (−) epicatechin gallate and (−) epigallocatechin gallate is isolated from one another. The process described in Hara '672 does not permit an economical production of EGCG on a technical scale because of the use of expensive column fillings. Furthermore, the process described in Hara '672 does not permit the production of EGCG, which may be added to food products because the solvent mixture used (i.e., acetone/tetrahydrofuran/chloroform) is not food-approved.

SUMMARY OF THE INVENTION

While the art describes the production of catechins as mixtures, there is still a need for a simple, safe, and economic process for producing EGCG in a purified form for incorporation as an ingredient into supplements and foodstuffs.

One object of the present invention is to provide a process for producing EGCG in a purified form for incorporation as an ingredient into supplements and foodstuffs.

Another object of the invention is a process to separate EGCG from a mixture of tea catechins and/or caffeine with improved selectivity when carrying out the separation using a macroporous polar resin and a suitable polar elution solvent.

Accordingly, one embodiment of the invention is a process for producing epigallocatechin gallate (EGCG) comprising the steps of:

a) providing a green tea extract;

b) subjecting the green tea extract to chromatography on a macroporous polar resin at a temperature between about 10° C. to about 80° C.; and c) eluting the EGCG from the macroporous polar resin with a polar elution solvent at a temperature between about 10° C. to about 80° C. and at a pressure between about 0.1 bar to about 50 bar.

DETAILED DESCRIPTION OF THE INVENTION

Thus, the present invention is directed to a process for producing epigallocatechin gallate (EGCG), which includes the steps of:

a) providing a green tea extract;

b) subjecting the green tea extract to chromatography on a macroporous polar resin at a temperature in the range of about 10° C. to about 80° C.;

c) eluting EGCG from the macroporous polar resin with a polar elution solvent at a temperature in the range of about 10° C. to about 80° C. and at a pressure in the range of about 0.1 bar to about 50 bar;

d) optionally concentrating the eluate of step c);

e) optionally regenerating the macroporous polar resin by desorbing the remaining catechins; and f) optionally concentrating the desorbed catechins of step e).

The production of the green tea extract used as starting material is well known in the art. For example, green tea leaves are typically extracted with hot or cold water to form a solution containing tea catechins and caffeine. This green tea solution may be further concentrated to form either a concentrated extract solution or a dry powder. The extract solution or the powder may contain stabilizers, such as food-approved acids, e.g. citric acid, ascorbic acid, isoascorbic acid, and the like.

Tea extract powders, such as green tea extract powders, are also commercially available from, for example, Guizhou Highyin Biological Product Co., Guiyang, P.R. China, or Zhejang Zhongke Plant Technical Co. Ltd., Hangzhou, Zhejang, P.R. China.

The separation of EGCG may be carried out by subjecting the green tea extract to a column filled with a macroporous polar resin.

As used herein, "macroporous polar resins" means acrylic resins, such as polyacrylates, e.g. AMBERLITE® XAD-7 (available from Rohm and Haas, Philadelphia, Pa.); polymethacrylates (such as e.g. AMBERCHROM® CG-71 available from Toso Haas or DIAION HP 2MG available from Mitsubishi Chem. Corp., Philadelphia, Pa.); polyamides (such as Polyamide 11 available from Merck, Darmstadt, Germany, Polyamide 6 and Nylon 6,6 available from Fluka, Buchs, Switzerland catalogue Nos. 02395 and 74712, respectively, and Polyamide 12, Grilamid L 25 natur, available from EMS Chemie, Domat, Switzerland); Polyvinylpyrrolidone P 6755 (available from Sigma); aromatic polyamides; and polyesters.

The resin is preferably operated degassed and equilibrated with the elution solvent.

The process according to the invention is performed at temperatures in the range of about 10° C. to about 80° C., preferably of about 40° C. to about 60° C. Thermostatic control may take place, for example, by placing the column in a thermostatically controlled area, such as, a heating jacket.

The hydraulic pressure under which the mobile phase is passed through the column may be varied within wide limits. The mobile phase is preferably pumped through the column at a pressure of about 0.1 bar to about 50 bar, preferably at about 0.1 bar to about 20 bar, such as, for example, at about 0.1 bar to about 10 bar.

The mobile phase includes a polar elution solvent which is a mixture of water and an organic solvent. As used herein, "organic solvent" means alcohols, such as methanol, ethanol, isopropanol and the like, and ketones, such as acetone or esters such as ethylacetate or mixtures thereof. The use of food grade alcohols, such as ethanol and isopropanol, is preferred. Particularly good results are obtained when using a mobile phase containing a mixture of about 70 vol % to about 95 vol %, preferably about 90 vol %, of water and about 5 vol % to about 30 vol %, preferably about 10 vol %, of organic solvent. It is advantageous to degas the mobile phase and keep it under an inert atmosphere, such as nitrogen or argon.

The column is conditioned with the mobile phase. The flow rate of the mobile phase through the column may be varied within wide limits. The flow rate is in the range of about 0.5 to about 20 bed volumes/hour, preferably about 0.5 to about 10 bed volumes/hour, such as about 0.8 to about 5 bed volumes/hour. (1 bed volume corresponds to 1 $m^3$ solution or solvent per $m^3$ resin).

After equilibrium has been established between the stationary and mobile phases, tea extract solution is introduced into the mobile phase, thus, subjecting the green tea extract to chromatography on the macroporous polar resin. If a green tea extract powder is used as the starting material, the powder is dissolved in the mobile phase. If an aqueous green tea extract is used, it is advantageous to adjust the ratio of water to organic solvent in the extract to that of the mobile phase by adding an organic solvent.

A key aspect of the present invention is to treat the green tea extract with a macroporous polar resin at temperatures in the range of about 10° C. to about 80° C., preferably at about 40° C. to about 60° C. and to elute EGCG with a polar elution solvent. This particular interplay of the three features of resin, eluent, and temperature forms an important aspect of the present invention and leads to a specific separation of EGCG from a mixture of tea catechins and/or caffeine, thus obtaining, after elution, an EGCG fraction containing at least 75%, preferably more than 85%, such as for example, about 90% to about 97%, of EGCG calculated based on the total amount of catechins present in the extract or concentrate.

The ability of the macroporous polar resin to absorb caffeine, EGCG and the remaining catechins is different depending also on the eluent used and the temperature. The affinity of the resin for caffeine is less than that for EGCG, thus, caffeine, if present, is eluted first and may be separated off. If appropriate, it is also possible to recover caffeine in a purified form using this process, which could be an economic advantage, too. A second fraction is isolated in which the EGCG is present. The remaining tea catechins show a stronger affinity for the resin than EGCG does, thus, remaining adsorbed until the resin is regenerated using a solvent which is able to desorb the remaining catechins. For example, the remaining catechins may be desorbed by eluting with a pure organic solvent or by changing the ratio of water to organic solvent in the mobile phase. A suitable regeneration solvent is, e.g., a pure organic solvent or a mixture of about 10 vol % to about 60 vol % of water and of about 40 vol % to about 90 vol % of organic solvent, preferably about 40 vol % of water and about 60 vol % of organic solvent.

The concentration of the EGCG in the eluate may be carried out by methods well known in the art, such as for example by evaporation. The EGCG eluate may be evaporated to dryness to form a powder containing EGCG in high purity or concentrated to allow crystallization. The concentration may be carried out by adding a stabilizer to the eluate such as a food-approved acid, e.g. citric acid, ascorbic acid, isoascorbic acid, and the like. The acid is preferably added in an amount of about 0.1 to about 2.5 vol % with respect to EGCG.

The pre-fraction containing the caffeine and the fraction of step e) containing the remaining catechins may be concentrated as described above.

The process may be carried out using a single column or a system of multiple chromatographic columns. The process may also be carried out using "simulated moving bed chromatography" or "annular chromatography," both of which are well known in the art.

The process of the present invention may be conducted with simple and economical operations, and is thus applicable to a large scale production in respect of yield and handling.

EGCG prepared as described above possesses a strong antioxidant activity and may be used as an antioxidant for various foodstuffs, cosmetics, oils, and the like. In addition, EGCG has an antimutagenic effect, an antibacterial effect, and a beneficial effect on cholesterol level in blood. Thus, concentrates or pure EGCG are useful in health care preparations.

The following example are provided to further illustrate the process of the present invention. These examples are illustrative only and are not intended to limit the scope of the invention in any way.

EXAMPLES

Example 1

Separation of EGCG

A green tea extract containing the different catechins and caffeine (manufactured by Guizhou Highyin Biological Products Co., Guiyang, China as "Green Tea Extract, min. 95% of polyphenols") was used as starting material. The concentration of the components in the green tea extract were determined by HPLC using UV absorbance and expressed as wt.-%. The content of EGCG, caffeine, other, catechins, as well as gallic acid in the starting material is shown in Table 1.

TABLE 1

Concentration of the tea components in the starting material

| Compound | Tea extract Example 1 HPLC/wt.-% | Tea extract Example 1 Relative Percentage/% |
|---|---|---|
| Gallic acid | 0.01 | 0.0 |
| Catechin | 2.3 | 3.2 |
| Caffeine | 11.0 | 15.1 |
| EGCG | 38.1 | 52.3 |
| Epicatechin | 5.2 | 7.11 |
| GCG | 6.6 | 9.1 |
| ECG | 9.7 | 13.3 |
| Total | 72.9 | 100 |

33.5 l (26 kg) of AMBERLITE® XAD-7 resin having a particle size of 0.3 to 1.2 mm were filled into a pilot scale column having an inner diameter of 150 mm, a length of 2 m and a volume of 35.4 l. The column was equipped with a heating jacket. The resin was thoroughly washed with water and equilibrated with a mixture of water/isopropanol (ratio 9:1 by volume). The apparatus and the solvents used were degassed and kept under an inert nitrogen atmosphere prior to use.

The temperature of the filled column was maintained at 60° C. 0.4 kg of the above green tea extract (Table 1) containing 152.5 g of pure EGCG were dissolved in 1.8 kg of a mixture of water/isopropanol (ratio 9:1 by volume) and applied to the top of the column. EGCG was eluted from the column by means of a pump under a pressure of 0.5 bar and at a temperature of 60° C. with a mixture of water/isopropanol (ratio 9:1 by volume) at a constant flow rate of 50 kg/hour. After an initial eluate of 144 kg (prefraction), a main eluate of 174 kg was collected containing 112 g of EGCG as the main polyphenol component. The EGCG concentration in the main eluate was 0.064 wt %. The yield of separated EGCG starting from 152.5 g EGCG in the tea extract was 73.5 wt %.

To regenerate the resin, the remaining catechins were desorbed by eluting with 78.3 kg of a mixture of water/isopropanol (ratio 4:6 by volume). Before the next separation, the column was conditioned with 86 kg of a mixture of water/isopropanol (ratio 9:1 by volume) in backwash mode at a flow rate of 120 kg/hour.

Table 2 illustrates the separation effect as shown by the relative percentage of EGCG. The concentration of the tea components in the main eluate was determined by HPLC using UV absorbance and expressed as wt.-% or ppm.

TABLE 2

Concentration of the tea components in the main eluate

| Compound | Main fraction Example 1 HPLC/ppm | Rel. Percentage/% |
|---|---|---|
| Gallic acid | 0 | 0.0 |
| Catechin | 21 | 3.1 |
| Caffeine | 1 | 0.1 |
| EGCG | 644 | 92.1 |
| Epicatechin | 29 | 4.1 |
| GCG | 3 | 0.4 |
| ECG | 1 | 0.1 |
| Total | 699 | 100 |

Example 2

Example 1 was repeated using another lot of the "Green tea extract, min. 95% of polyphenols" from Guizhou Highyin Biological Products Co. which contained the components shown in Table 3.

TABLE 3

Concentration of the tea components in the starting material

| Compound | Tea extract Example 2 HPLC/wt.-% | Tea extract of Example 2 Rel. Percentage/% |
|---|---|---|
| Gallic acid | 0.1 | 0.1 |
| Catechin | 1.4 | 1.9 |
| Caffeine | 13.8 | 18.8 |
| EGCG | 35.1 | 47.9 |
| Epicatechin | 3.3 | 4.5 |
| GCG | 8.2 | 11.2 |
| ECG | 11.4 | 15.6 |
| Total | 73.2 | 100 |

The washed column of Example 1 was maintained at 60° C., and used to carry out the separation. 0.4 kg of the above green tea extract (Table 3) containing 140.5 g of pure EGCG were dissolved in 1.8 kg of a mixture of water/isopropanol (ratio 9:1 by volume) and applied to the top of the column. The column was then eluted as described in Example 1. After an initial eluate of 200 kg (prefraction), a main eluate of 117 kg was collected containing 72.8 g of EGCG as the main polyphenol component. The EGCG concentration in the main eluate was 0.062 wt %. The yield of separated EGCG starting from 140.5 g of EGCG in the tea extract was 51.8 wt %.

To regenerate the resin, the remaining catechins were desorbed by eluting with 100 kg of a mixture of water/isopropanol (ratio 4:6 by volume). Before the next separation step, the column was conditioned with 100 kg of a mixture of water/isopropanol (ratio 9:1 by volume) in backwash mode at a flow rate of 120 kg/hour.

Table 4 illustrates the separation effect as shown by the relative percentage of EGCG in the main eluate. The concentration of the tea components in the main eluate was determined by HPLC using UV absorbance and expressed as ppm. Compared to Example 1, EGCG was obtained in a higher percentage.

TABLE 4

Concentration of the tea components in the main eluate

| Compound | Main fraction Example 2 HPLC/ppm | Rel. Percentage/% |
|---|---|---|
| Gallic acid | 0 | 0.0 |
| Catechin | 10 | 1.6 |
| Caffeine | 1 | 0.2 |
| EGCG | 622 | 96.4 |
| Epicatechin | 2 | 0.3 |
| GCG | 6 | 0.9 |
| ECG | 4 | 0.6 |
| Sum | 645 | 100 |

Example 3

Concentration of the Eluate 9008 kg of the eluate of the adsorption/desorption column prepared by repeated runs as described in Example 2 were stabilized by addition of 2% citric acid, calculated on the EGCG amount. The eluate was concentrated at a temperature of 40° C. and a pressure of 55 mbar using a falling film evaporator made from stainless steel with a heat exchange surface area of 1.1 m². The amount of catechins and caffeine of the feed solution subjected to the evaporation unit is given in Table 5.

TABLE 5

Concentration of the tea components in the purified EGCG solution subjected to evaporation

| Compound | Feed Falling film evaporator HPLC/ppm | Rel. Percentage/% |
|---|---|---|
| Gallic acid | 0 | 0.0 |
| Catechin | 10 | 1.4 |
| Caffeine | 1 | 0.1 |
| EGCG | 712 | 96.2 |
| Epicatechin | 7 | 0.9 |
| GCG | 7 | 0.9 |
| ECG | 3 | 0.4 |
| Total | 740 | 100 |

The feed flow to the evaporator was regulated to a flow rate in the range of 120 kg/hour to 130 kg/hour at a recycle flow rate of 300 kg/hour. Thus, the distillate flow rate was 123.5 kg/hour at a bottom product removal rate of 0.52 kg/hour. During the concentration process, a first fraction was sampled and analyzed, followed by a second fraction which was also analyzed. The two fractions of EGCG concentrates had a total mass of 63.5 kg.

Table 6 shows the concentration of the tea components in the bottom products. The recovery of EGCG was 95.9%. The analytical result clearly indicates that the high purity of the separated EGCG could be maintained during the concentration of the solution.

EGCG may be isolated from the concentrated solution in a solid form either by spray drying or by crystallization.

TABLE 6

Concentration of the tea components in the EGCG concentrate from the falling film evaporator

| | Bottom product of falling film evaporator | | | |
|---|---|---|---|---|
| | Composition 1st fraction | | Composition 2nd fraction | |
| Compounds | HPLC/wt.-% | Rel. Percentage | HPLC/wt.-% | Rel. Percentage |
| Gallic acid | 0.00 | 0.0 | 0.00 | 0.0 |
| Catechin | 0.17 | 1.5 | 0.14 | 1.6 |
| Caffeine | 0.01 | 0.1 | 0.02 | 0.2 |
| EGCG | 10.70 | 95.4 | 8.07 | 94.8 |
| Epicatechin | 0.16 | 1.4 | 0.11 | 1.3 |
| GCG | 0.13 | 1.2 | 0.13 | 1.5 |
| ECG | 0.05 | 0.4 | 0.04 | 0.5 |
| Sum | 11.22 | 100 | 8.51 | 100 |
| Total mass of solution | 39.0 kg | | 24.5 kg | |

Example 4

450 ml of AMBERCHROM® CG-71c having a mean particle diameter of 120 microns were filled into a laboratory chromatography column made from stainless steel having an inner diameter of 2.2 cm and a length of 103 cm. The column was equipped with a heating jacket. The resin was washed and equilibrated with a mixture of water/ethanol (ratio 9:1 by volume)

20 g of a concentrated catechin powder "Green tea extract, min. 95% of polyphenols" from Guizhou Highyin Biological Products Co. (starting material) were dissolved in 20 ml of a mixture of water/ethanol (ratio 9:1 by volume). Afterwards, 14 g of this solution (corresponding to 2.99 g of EGCG) were applied to the top of the column. EGCG was eluted by means of a chromatographic pump under a pressure of 2–3 bar at a temperature of 60° C. with a mixture of water/ethanol (ratio 9:1 by volume) under a constant flow rate of 16 ml/minute. The eluent was degassed and maintained under a nitrogen atmosphere prior to use. After an initial eluate of 2.48 l (prefraction), the flow rate was changed to 25.5 ml/minute and the main eluate of 5.40 l was collected containing EGCG in a concentration of 0.627 g/l. With respect to other catechins and caffeine, the purity of the EGCG in the main eluate determined by HPLC, and expressed as relative percentage was 97.13%. During the experiment, the pressure in the system varied from 2 to 3 bar depending on the flow rate applied.

Table 7 compares the concentration of the tea components in the eluate and in the starting material, thus illustrating the separation effect as shown by the relative percentage of EGCG. The concentration of the tea components in the starting material and in the main fraction was determined by HPLC using UV absorbance and expressed as wt.-% or ppm.

TABLE 7

Separation on AMBERCHROM® CG-71c, 60° C., solvent system: water/ethanol

| Compound | Tea Concentrate (starting material) Example 4 HPLC/ wt.-% | Rel. Percentage/% | Main Fraction Example 4 HPLC/ ppm | Rel. Percentage/% |
|---|---|---|---|---|
| Gallic acid | 0.08 | 0.1 | 0 | 0.0 |
| Catechin | 0.50 | 0.6 | 1 | 0.2 |
| Caffeine | 9.29 | 11.3 | 5 | 1.2 |
| EGCG | 42.23 | 51.4 | 407 | 97.1 |
| Epicatechin | 4.24 | 5.2 | 3 | 0.7 |
| GCG | 8.09 | 9.9 | 1 | 0.2 |
| ECG | 17.70 | 21.6 | 2 | 0.5 |
| Total | 82.13 | 100 | 419 | 100 |

TABLE 8

Separation on AMBERLITE® XAD-7, 60° C., solvent system: water/ethanol

| Compound | Tea Concentrate (starting material) Example 5 HPLC/ wt.-% | Rel. Percentage/% | Main Fraction Example 5 HPLC/ ppm | Rel. Percentage/% |
|---|---|---|---|---|
| Gallic acid | 0.09 | 0.1 | 0 | 0.0 |
| Catechin | 0.50 | 0.6 | 2 | 0.4 |
| Caffeine | 9.17 | 11.5 | 7 | 1.3 |
| EGCG | 41.16 | 51.5 | 470 | 86.1 |
| Epicatechin | 4.16 | 5.2 | 5 | 0.9 |
| GCG | 7.75 | 9.7 | 22 | 4.0 |
| ECG | 17.16 | 21.5 | 40 | 7.3 |
| Total | 79.99 | 100 | 546 | 100 |

Example 5

450 ml of AMBERLITE® XAD-7, having a particle diameter of 0.3 to 1.2 mm was packed into a laboratory chromatography column made of glass having an inner diameter of 2.4 cm and a length of 100 cm. The column was equipped with a heating jacket and on the bottom with a glass sinter frit P3. The resin was thoroughly washed with deionized water and equilibrated with a mixture of water/ethanol (ratio 9:1 by volume) prior to use.

20 g of a concentrated catechin powder "Green tea extract, min. 95% of polyphenols" from Guizhou Highyin Biological Products Co. (starting material) were dissolved in 20 ml of a mixture of water/ethanol (ratio 9:1 by volume). Afterwards, 14 g of this solution (corresponding to 2.91 g of EGCG) were applied to the top of the column. EGCG was eluted with a mixture of water/ethanol (ratio 9:1 by volume) with a constant flow rate of 16.9 ml/minute at a temperature of 60° C. and a pressure of 0.5 to 1 bar. The eluent was degassed and maintained in a nitrogen atmosphere prior to use. After an initial eluate of 2.48 l (prefraction), the flow rate was changed to 23.6 ml/minute and the main eluate of 4.95 l was collected containing EGCG in a concentration of 0.470 g/l. With respect to other main catechins and caffeine, the purity of the EGCG in the main fraction determined by HPLC was 86.22% (see Table 8). The yield based on EGCG was 79.8%. During the experiment, the pressure in the system varied from 0.5 to 1 bar depending on the flow rate applied.

To regenerate the resin, the remaining catechins were desorbed by eluting with 1.35 l of a mixture of water/ethanol (ratio 4:6 by volume) at a flow rate of 22.5 ml/minute. This fraction can also be used for further purification or separation of the desorbed catechins. Table 8 compares the concentration of the tea components in the eluate and in the starting material, thus illustrating the separation effect as shown by the relative percentage of EGCG. The concentration of the tea components in the starting material and in the main fraction was determined by HPLC using UV absorbance and expressed as wt % or ppm.

Example 6

The regenerated resin of Example 5 was equilibrated in the laboratory column described in Example 5 by pumping a mixture of water/ethanol (ratio 9:1 by volume) through the resin.

20 g of a concentrated catechin powder "Green tea extract, min. 95% of polyphenols" from Guizhou Highyin Biological Products Co. (starting material) were dissolved in 20 ml of a mixture of water/ethanol (ratio 9:1 by volume). Afterwards, 14 g of this solution (corresponding to 3.04 g of EGCG) were applied to the top of the column. EGCG was eluted with a mixture of water/ethanol (ratio 9:1 by volume) with a constant flow rate of 22.5 ml/minute at a column temperature of 40° C. and a pressure of 1 to 2 bar. The eluent was degassed and maintained under a nitrogen atmosphere prior to use. After an initial eluate of 3.60 l (prefraction) the flow rate was changed to 26.3 ml/minute and the main eluate of 4.73 l was collected. The EGCG concentration in the main eluate was 0.278 g/l. With respect to other main catechins and caffeine, the purity of the epigallocatechin gallate in the main eluate determined by HPLC was 93.2%. The yield based on EGCG was 42.8%. During the experiment, the pressure in the system varied from 1 to 2 bar depending on the flow rate applied.

To regenerate the resin, the remaining catechins were desorbed by eluting with 1.98 l of a mixture of water/ethanol (ratio 4:6 by volume) at a flow rate of 26.3 ml/minute and a temperature of 40° C. This fraction may also be used for further purification or separation of the desorbed catechins. Table 9 compares the concentration of the tea components in the eluate and in the starting material, thus illustrating the separation effect as shown by the relative percentage of EGCG. The concentration of the tea components in the starting material and in the main fraction was determined by HPLC using UV absorbance and expressed as wt.-% or ppm.

TABLE 9

Separation on AMBERLITE ® XAD-7, 40° C., solvent system: water/ethanol

| Compound | Tea Concentrate (starting material) of Example 6 | | Main Fraction Example 6 | |
|---|---|---|---|---|
| | HPLC/ wt.-% | Rel. Percentage/% | HPLC/ ppm | Rel. Percentage/% |
| Gallic acid | 0.08 | 0.1 | 0 | 0.0 |
| Catechin | 0.51 | 0.6 | 3 | 1.0 |
| Caffeine | 9.48 | 11.3 | 4 | 1.4 |
| EGCG | 43.01 | 51.4 | 276 | 93.2 |
| Epicatechin | 4.34 | 5.2 | 9 | 3.0 |
| GCG | 8.23 | 9.8 | 2 | 0.7 |
| ECG | 18.03 | 21.5 | 2 | 0.7 |
| Total | 83.68 | 100 | 296 | 100 |

TABLE 10

Separation on AMBERLITE ® XAD-7, 60° C., Solvent system: water/isopropanol

| Compound | Tea Concentrate (starting material) of Example 7 | | Main Fraction Example 7 | |
|---|---|---|---|---|
| | HPLC/ wt.-% | Rel. Percentage/% | HPLC/ ppm | Rel. Percentage/% |
| Gallic acid | 0.05 | 0.1 | 0 | 0.0 |
| Catechin | 0.38 | 0.4 | 8 | 0.7 |
| Caffeine | 9.48 | 10.8 | 28 | 2.4 |
| EGCG | 45.42 | 51.8 | 998 | 85.7 |
| Epicatechin | 4.38 | 5.0 | 16 | 1.4 |
| GCG | 8.80 | 10.0 | 35 | 3.0 |
| ECG | 19.12 | 21.8 | 80 | 6.9 |
| Total | 87.63 | 100 | 1165 | 100 |

Example 7

The regenerated resin of Example 6 was equilibrated with a mixture of water/isopropanol (ratio 9:1 by volume)

20 g of a concentrated catechin powder "Green tea extract, min. 95% of polyphenols" from Guizhou Highyin Biological Products Co. (starting material) were dissolved in 20 ml of a mixture of water/isopropanol (ratio 9:1 by volume) by volume. Afterwards, 14 g of this solution (corresponding to 3.21 g of EGCG) were applied to the top of the column, and eluted with a mixture of water/isopropanol (ratio 9:1 by volume) with a constant flow rate of 18 ml/minute at a column temperature of 60° C. The eluent was degassed and maintained under a nitrogen atmosphere prior to use. After an initial eluate of 1.35 l (prefraction), the flow rate was changed to 16.5 ml/minute and a main eluate of 2.03 l was collected. The EGCG concentration in the main eluate was 0.998 g/l. With respect to other main catechins and caffeine, the purity of the epigallocatechin gallate in the main eluate determined by HPLC was 85.7%. The yield based on EGCG was 62.8%. During the experiment, the pressure in the system varied from 1 to 2 bar depending on the flow rate applied.

To regenerate the resin, the remaining catechins were desorbed by eluting with 2.03 l of a mixture of water/isopropanol (ratio 4:6 by volume) at a flow of 16.5 ml/minute and a temperature of 40° C. This fraction may also be used for further purification or separation of the desorbed catechins. Table 10 compares the concentration of the tea components in the eluate and in the starting material, thus illustrating the separation effect as shown by the relative percentage of EGCG. The concentration of the tea components in the starting material and in the main fraction was determined by HPLC using UV absorbance and expressed as wt.-% or ppm.

Example 8

The regenerated resin of Example 7 was equilibrated with a mixture of water/isopropanol (ratio 9:1 by volume).

20 g of a concentrated catechin powder "Green tea extract, min. 95% of polyphenols" from Guizhou Highyin Biological Products Co. (starting material) were dissolved in 20 ml of a mixture of water/isopropanol (ratio 9:1 by volume). Afterwards, 14 g of this solution (corresponding to 3.10 g of EGCG) were applied to the top of the column. EGCG was eluted with a mixture of water/isopropanol (ratio 9:1 by volume) with a constant flow of 16.9 ml/minute at a column temperature of 40° C. The eluent was degassed and maintained under a nitrogen atmosphere prior to use. After an initial eluate of 2.48 l (prefraction), the flow rate was changed to 23.66 ml/minute and a main eluate of 4.95 l was collected. The EGCG concentration in the main eluate was 0.370 g/l. With respect to other main catechins and caffeine, the purity of the EGCG in the main fraction determined by HPLC was 86.6%. The yield based on EGCG was 59.2%. During the experiment, the pressure in the system varied from 1 to 2 bar depending on the flow rate applied.

To regenerate the resin, the remaining catechins were desorbed by eluting with 2.03 l of a mixture of water/isopropanol (ratio 4:6 by volume) at a flow rate of 16.5 ml/minute and a temperature of 40° C. This fraction can also be used for further purification or separation of the desorbed catechins.

Table 11 compares the concentration of the tea components in the eluate and in the starting material, thus illustrating the separation effect as shown by the relative percentage of EGCG. The concentration of the tea components in the starting material and in the main fraction was determined by HPLC using UV absorbance and expressed as wt.-% or ppm.

TABLE 11

Separation on AMBERLITE ® XAD-7, 40° C.,
Solvent system: water/isopropanol

| Compound | Tea concentrate (starting material) of Example 8 | | Main fraction of Example 8 | |
|---|---|---|---|---|
| | HPLC/ wt-% | Rel. Percentage/% | HPLC/ ppm | Rel. Percentage/% |
| Gallic acid | 0.20 | 0.2 | 0 | 0.0 |
| Catechin | 0.49 | 0.6 | 4 | 0.9 |
| Caffeine | 9.21 | 10.8 | 6 | 1.4 |
| EGCG | 43.74 | 51.5 | 370 | 86.4 |
| Epicatechin | 4.23 | 5.0 | 14 | 3.3 |
| GCG | 8.50 | 10.0 | 11 | 2.6 |
| ECG | 18.52 | 21.8 | 23 | 5.4 |
| Total | 84.89 | 100 | 428 | 100 |

Example 9

Separation of EGCG over Polyamide 11 Using Organic Solvents

A commercially available green tea extract ("Green tea extract, min. 95% of polyphenols," Lot #960328 from Guizhou Highyin Biological Product Co., Guiyang, China) containing catechins and caffeine in an amount as shown in Table 12 was used as the starting material. The concentration of the tea components in the starting material was determined by HPLC using UV absorbance.

TABLE 12

Concentration of tea components in the starting material

| Compound | Tea extract HPLC/wt.-% | Tea extract Rel. Percentage/% |
|---|---|---|
| Gallic acid | 0.01 | 0.0 |
| EGC | 2.02 | 3.0 |
| Catechin | 0.78 | 1.2 |
| Caffeine | 8.48 | 12.5 |
| EGCG | 36.87 | 54.5 |
| Epicatechin | 4.48 | 6.6 |
| GCG | 4.77 | 7.1 |
| ECG | 10.22 | 15.1 |
| Total | 67.63 | 100 |

250 g of a commercially available Polyamide 11 (Cat. No. 1.07435.0100, origin Merck, Darmstadt, Germany) having a particle size of 5–40 microns were suspended in 300 ml ethyl acetate and transferred into a column having an inner diameter of 5 cm and a length of 36 cm. The column was equipped with a heating jacket and heated to 40° C. 3 g of the starting green tea extract, characterized in Table 12, containing 1.11 g of pure EGCG were dissolved in 153 ml of ethyl acetate and applied to the top of the column. An ethyl acetate/ethanol gradient elution (500 ml ethyl acetate, 1000 ml ethyl acetate/ethanol (8.5:1.5 v/v), 1000 ml ethyl acetate/ethanol (7:3 v/v), 2000 ml ethyl acetate/ethanol (1:1 v/v)) under a pressure of 0.3 bar afforded a main fraction of 550 ml, which after evaporation of the solvents gave 1.12 g of solid containing 0.87 g EGCG as the main catechin component. The EGCG concentration in the main eluate was 0.186%. The yield of separated EGCG calculated from 1.106 g EGCG present in the starting tea extract was 76%.

To regenerate the resin, elution with 500 ml ethanol desorbed the remaining catechins. Before the next separation, the column was conditioned with 500 ml of ethyl acetate.

Table 13 illustrates the separation effect. The concentration of the tea components in the main eluate was determined by HPLC using UV absorbance.

TABLE 13

Concentration of tea components in the residue of the main eluate (after solvent evaporation)

| Compound | Residue of main fraction HPLC/wt.-% | Residue of main fraction Rel. Percentage/% |
|---|---|---|
| Gallic acid | 0 | 0 |
| EGC | 0 | 0 |
| Catechin | 0 | 0 |
| Caffeine | 0 | 0 |
| EGCG | 77.40 | 96.4 |
| Epicatechin | 0.05 | 0.1 |
| GCG | 0.74 | 0.9 |
| ECG | 2.07 | 2.6 |
| Total | 80.26 | 100 |

Example 10

Separation of EGCG over Polyamide 11 Using an Aqueous Solvent Mixture

An aqueous green tea extract solution containing catechins and caffeine in an amount as shown in Table 14 was used as the starting material. The concentration of the tea components was determined by HPLC using UV absorbance and expressed in wt.-%

TABLE 14

Concentration of the tea components in the residue of the starting tea extract solution (after solvent evaporation)

| Compound | Tea extract HPLC/wt.-% | Tea extract Rel. Percentage/% |
|---|---|---|
| Gallic acid | 1.36 | 4.8 |
| EGC | 3.61 | 12.6 |
| Catechin | 1.45 | 5.1 |
| Caffeine | 6.89 | 24.1 |
| EGCG | 10.14 | 35.5 |
| Epicatechin | 1.59 | 5.6 |
| GCG | 0.99 | 3.5 |
| ECG | 2.51 | 8.8 |
| Total | 28.54 | 100 |

25 g of Polyamide 11 (Cat. No. 1.07435.0100, origin Merck, Darmstadt, Germany) having a particle size of 5–40 microns were suspended in 100 ml water, and the pH adjusted to 6.5. This suspension was transferred into a column having an inner diameter of 3 cm and a length of 8 cm. 10 ml of the above green tea extract (Table 14) containing 0.078 g of pure EGCG were applied to the top of the column. A water/ethanol gradient elution (500 ml water, 600 ml water/ethanol (7:3 v/v), 350 ml water/ethanol (6:4 v/v), 500 ml water/ethanol (1:1 v/v)) with a flow rate of 5 ml/minute afforded a main fraction of 110 ml (0.072 g) containing 0.046 g EGCG. The EGCG concentration in the main eluate was 0.06%. The yield of separated EGCG starting from 0.078 g EGCG in the tea extract was 59%.

To regenerate the resin, elution with 500 ml ethanol desorbed the remaining catechins. Before the next separation, the column was conditioned with 500 ml of water.

Table 15 illustrates the separation effect. The concentration of the tea components in the main eluate was determined by HPLC using UV absorbance.

TABLE 15

Concentration of the tea components in the residue of the main fraction (after solvent evaporation)

| Compound | Residue of main fraction HPLC/wt.-% | Residue of main Fraction Rel. Percentage/% |
|---|---|---|
| Gallic acid | 1.10 | 1.6 |
| EGC | 0.00 | 0.0 |
| Catechin | 1.29 | 1.9 |
| Caffeine | 0.00 | 0.0 |
| EGCG | 63.53 | 91.7 |
| Epicatechin | 0.00 | 0.0 |
| GCG | 0.16 | 0.2 |
| ECG | 3.20 | 4.6 |
| Total | 69.28 | 100 |

Example 11

Separation of EGCG over AMBERLITE® XAD-7, Solvent System: Water/Ethanol 416 ml AMBERLITE® XAD-7 resin having a mean particle diameter between 0.3 and 1.2 mm were filled into a laboratory chromatography column made from glass (ECO 25/999 M3V-K from Stagroma AG, Wallisellen, Switzerland) having an inner diameter of 2.5 cm and a length of 100 cm. The column was equipped with a heating jacket and heated to 60° C. The resin was washed and equilibrated with a mixture of water/ethanol (ratio 9:1 by volume).

A commercially available green tea extract ("Tea polyphenols TP-80" from Zhejang Zhongke Plant Technical Co. Ltd., Hangzhou, Zhejang, P.R. China) containing catechins and caffeine in an amount as shown in Table 16 was used as the starting material.

The concentration of the tea components in the starting material was determined by HPLC using UV absorbance and expressed in wt.-%.

TABLE 16

Concentration of tea components in the starting material

| Compound | Tea extract HPLC/wt.-% | Tea extract Rel. Percentage/% |
|---|---|---|
| Gallic acid | 0.1 | 0.1 |
| EGC | 8.6 | 10.1 |
| Catechin | 1.9 | 2.2 |
| Caffeine | 6.2 | 7.3 |
| EGCG | 40.3 | 47.4 |
| Epicatechin | 10.4 | 12.2 |
| GCG | 0.9 | 1.1 |
| ECG | 16.6 | 19.5 |
| Total | 85.0 | 100 |

11.2 g of the starting green tea extract, characterized in Table 16, containing 4.5 g of pure EGCG were dissolved in 112.5 ml of deionized water and applied to the top of the column.

The catechins were eluted with a mixture of water/ethanol (ratio 9:1 by volume) with a constant flow rate of 0.6 l/hour at a column temperature of 60° C. The eluent was degassed and maintained under a nitrogen atmosphere prior to use.

After an initial eluate of 1.2 l, the composition of the eluent was changed to water/ethanol at a ratio of 8:2 by volume. This elution with a total amount of 1.5 l afforded a main fraction of 900 ml containing 2.115 g EGCG. The EGCG concentration in the main fraction was 0.245%. The yield of separated EGCG starting from 4.5 g EGCG in the tea extract was 47%. During the experiment, the pressure in the system varied from 0.8 to 1.5 bar.

To regenerate the resin, the elution was continued with a mixture of water/ethanol 4:6 by volume, thus ethanol desorbed the remaining catechins. Before the next separation, the column was conditioned with water/ethanol 9:1 by volume.

Table 17 illustrates the separation effect. The concentration of the tea components in the residue of the main fraction (after evaporation of the solvent) was determined by HPLC using UV absorbance and expressed as wt.-%.

TABLE 17

Concentration of tea components in the residue of the main fraction (after solvent evaporation)

| Compound | Residue of main fraction HPLC/wt.-% | Residue of main fraction Rel. Percentage/% |
|---|---|---|
| Gallic acid | 0 | 0 |
| EGC | 0 | 0 |
| Catechin | 0.6 | 0.7 |
| Caffeine | 0.3 | 0.3 |
| EGCG | 81.4 | 94.5 |
| Epicatechin | 1.7 | 2.0 |
| GCG | 0.2 | 0.2 |
| ECG | 1.9 | 2.2 |
| Total | 86.1 | 100 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing (−)-epigallocatechin gallate (EGCG) comprising the steps of:
    a) providing a green tea extract containing tea catechins and caffeine;
    b) subjecting the green tea extract to chromatography on a macroporous polar resin at a temperature between about 40° C. to about 60° C.; and
    c) eluting the EGCG from the macroporous polar resin with a polar elution solvent at a temperature between about 40° C. to about 60° C. and at a pressure between about 0.1 bar to about 50 bar.

2. A process according to claim 1 further comprising concentrating the eluate of step c).

3. A process according to claim 1 further comprising regenerating the macroporous polar resin by desorbing any remaining catechins from the resin.

4. A process according to claim 3 further comprising concentrating the desorbed catechins.

5. A process according to claim 1 wherein the macroporous paler resin is selected from the group consisting of polyacrylate resins, polymethacrylate resins, polyamide resins, and polyester resins.

6. A process according to claim 5 wherein the macroporous polar resin is a polyacrylate or polymethacrylate resin.

7. A process according to claim 5 wherein the polyamide resin is Polyamide 11.

8. A process according to claim 1 wherein steps b) and c) are carried out at a temperature between about 20° C. to about 60° C.

9. A process according to claim 8 wherein the temperature is between about 40° C. to about 60° C.

10. A process according to claim 1 wherein step c) is carried out under a pressure of about 0.1 bar to about 20 bar.

11. A process according to claim 10 wherein the pressure is about 0.1 bar to about 10 bar.

12. A process according to claim 1 wherein the polar elution solvent is a mixture of water and an organic solvent.

13. A process according to claim 12 wherein the elution solvent is a mixture of about 70 vol % to about 95 vol % of water and about 5 vol % to about 30 vol % of an organic solvent.

14. A process according to claim 13 wherein the elution solvent is a mixture of about 90 vol % of water and about 10 vol % at an organic solvent.

15. A process according to claim 12 wherein the organic solvent is selected from the group consisting of ethanol, isopropanol, ethyl acetate, and acetone.

16. A process according to claim 1 wherein the elution of step c) is carried out at a flow rate in the range of about 0.5 to about 20 bed volumes/hour.

17. A process according to claim 16 wherein the elution is carried out at a flow rate in the range of about 0.5 to about 10 bed volumes/hour.

18. A process according to claim 17 wherein the elution is carried out at a flow rate in the range of about 0.8 to about 5 bed volumes/hour.

19. A process according to claim 1 further comprising concentrating an eluate from step a) by adding to the eluent an acid selected from the group consisting of citric acid, ascorbic acid, and isoascorbic acid.

20. A process according to claim 19 wherein the amount of acid added to the eluent is about 0.1 wt % to about 2.5 wt % with respect to EGCG.

21. A process according to claim 2 wherein the concentrating step is carried out with a pure organic solvent.

22. A process according to claim 21 wherein the organic solvent consists of essentially about 10 vol % to about 60 vol % of water and about 40 vol % to about 90 vol % of an organic solvent.

23. A process according to claim 22 wherein the solvent consists of essentially of a mixture of about 40 vol % of water and about 60 vol % of an organic solvent.

* * * * *